United States Patent [19]

Steele

[11] 4,166,698
[45] Sep. 4, 1979

[54] SECONDARY LIGHT TESTING IN OPTICAL SMOKE DETECTORS

[75] Inventor: Donald F. Steele, Cohasset, Mass.

[73] Assignee: American District Telegraph Company, Jersey City, N.J.

[21] Appl. No.: 805,512

[22] Filed: Jun. 10, 1977

[51] Int. Cl.² ........................................... G01N 21/00
[52] U.S. Cl. ..................................... 356/338; 250/574; 340/630
[58] Field of Search ................. 356/103, 104; 250/574; 340/630

[56] References Cited

U.S. PATENT DOCUMENTS

| | | | |
|---|---|---|---|
| 2,877,453 | 3/1959 | Mendenhall, Jr. | 356/103 |
| 3,598,492 | 8/1971 | Fruengel | 356/103 |
| 3,868,184 | 2/1975 | Marsocci | 356/103 |
| 4,025,915 | 5/1977 | Enemark | 250/574 |
| 4,053,785 | 10/1977 | Lee et al. | 250/574 |

*Primary Examiner*—Conrad J. Clark
*Attorney, Agent, or Firm*—James H. Grover

[57] ABSTRACT

One type of smoke detector has a housing forming a dark chamber into which light is directed on a path viewed by a smoke sensing photocell. Smoke in the viewed light path scatters light to the cell exciting the cell to alarm state if the smoke is of density predetermined to be dangerous. The detector is tested for its ability to respond to the predetermined smoke density by means of an external owner-operated button. Depressing the button turns a lever or bell crank which intercepts the light path in the chamber and scatters light to one or more large areas within the dark chamber. These secondary areas in turn rescatter the scattered light to the photocell simulating smoke and exciting the cell to alarm state.

The primary light scattering surface of the bell crank and the areas of secondary light scatter are large enough that the light ultimately scattered to the photocell is equivalent to that scattered by smoke of the predetermined density.

14 Claims, 5 Drawing Figures

SECONDARY LIGHT TESTING IN OPTICAL SMOKE DETECTORS

BACKGROUND OF THE INVENTION

Reference is made to U.S. Pat. No. 3,868,184 and to my copending U.S. patent application Ser. No. 777,043, filed Mar. 14, 1977, which are incorporated herein by reference.

In the above mentioned patent there is shown an optical smoke detector with an owner-operated bell crank carrying a thin wire. In testing the smoke detector the wire is swung through the smoke detection zone where the light path from the exciting source and the view of the photocell coincide. Light is then scattered directly from the test wire to the photocell. Such a test wire can simulate a predetermined density of smoke satisfactorily but has the disadvantage of being very fine and flexible making it difficult to see and handle during manufacture. A larger wire would be less critical as to its location with respect to the light beam and photocell and the reflectance of its surface, but would also scatter far more light than smoke particles.

Accordingly it is the object of the present invention to provide a smoke detector with testing means which need not include a fine, fragile wire and which scatters light in a manner more representative of smoke.

STATEMENT OF INVENTION

According to the invention an optical particle detector comprises a smoke accessible dark chamber, a source of light projected on a path in the chamber, a photocell disposed to view an area within the chamber and responsive to light scattered by particles in the path, and actuated means outside the view of the photocell for directing light onto the viewed area in the enclosure for secondary light scattering from said area toward the photocell thereby to simulate particles in the chamber. By the term means for directing light it is meant to include means for scattering or reflecting light from a primary source as well as directing light directly from a source onto a secondary scattering area.

DRAWINGS

DESCRIPTION

Figure 1:
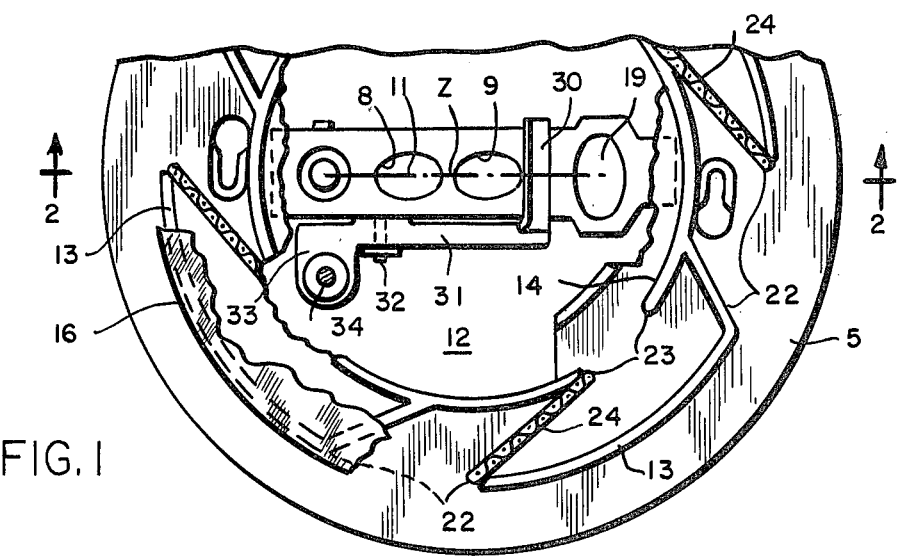
FIG. 1 is a plan view, partly broken away of one form of optical smoke detector according to the invention.
Figure 2:
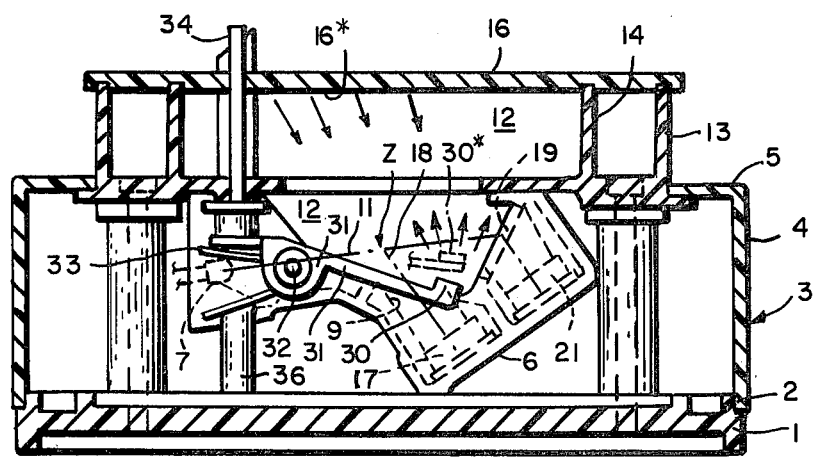
FIG. 2 is a section on line 2—2 of FIG. 1.

The optical smoke detector shown in FIGS. 1 and 2, described in greater detail in my aforementioned application Ser. No. 777,043, comprises a circular base plate 1 with a flange 2 over which fits a circular housing 3. The housing 3 includes a lower peripheral wall 4 with a face 5 around an optical block 6. The block 6 contains a light emitting diode source (LED) 7, a smoke sensing photocell 17 and a compensating photocell 21. Light from the LED source 7 radiates through a passage 8 in the optical block on a path indicated by the axis 11, it being understood that the light path is a diverging cone along the axis 11. The light path extends into a dark chamber 12 surrounded by the housing 3 as so far described. Additionally the housing includes a superstructure comprising exterior walls 13, interior walls 14 arising above the face 5, and a cover 16 over the walls 13 and 14. The dark chamber 12 thus includes the space within the walls 13 and 14 and the cover 16.

The smoke sensing photocell 17 views the light path 11 through a passage 9 in the block 6 along an axis 18, and also views the interior of the dark chamber 12 at areas such as the underside of the cover 16 and the walls of its passage 9. Smoke can enter into the dark chamber 12 through screens 24 inclined between outer smoke inlet ports 22 in the exterior walls 13 and the inner inlet ports 23 in the interior walls 14. These inlets and the dark chamber are formed of plastic or other material with an anti-reflecting, black surface so as to reduce the exciting effect of light outside the smoke detector upon the smoke sensing cell 17 within the chamber 12. However, it is a part of the present invention that, despite measures to eliminate light reflection the various surfaces of the dark chamber 12 will retain a light scattering property, although a weak one.

According to the present invention, as shown in FIGS. 1 and 2, a light scattering flag 30 is mounted on a bell crank 31 pivoted at 32 on the optical block 6. The extended arms 33 of a spring coiled about the pivot 32 normally hold the flag 30 in the position shown abutting the optical block 6, out of the light path 11 and the view 18 of the smoke sensing photocell 17. A plunger 34 extending from outside the cover 16 of the detector to one end of the bell crank 31 can be actuated by the owner or operator of the detector so as to rotate the bell crank and move the flag 30 into the cone of light along the axis 11 from the LED light source 7.

As shown particularly in FIG. 1 the flag 30 is substantially larger in surface area that the fine wire of the previously cited patent. Moreover, as in FIG. 2, a stop 36 is located in the path of the bell crank so as to limit movement of the flag 30 to a position 30* shown in broken lines, which position is in the light path from the LED 7 but is substantially out of the view of the smoke sensing photocell 17. In the broken line position 30* the flag scatters no or an insignificant amount of light directly to the smoke sensing cell 17, although a minor amount of light may be scattered to the wall 9 leading to the photocell 17. However, as shown by arrows emanating from the primary scattering surface of the flag at 30*, the surface of the flag scatters a substantial amount of light diffusely to secondary light scattering areas in the upper portions of the dark chamber including the internal area of the face 5 and area 16* of the cover 16. These secondary light scattering areas, which are substantially larger than the primary scattering surface by a factor of several thousand, in turn rescatter light received from the flag 30* in various directions including those of the arrows emanating downwardly from the underside area 16* of the cover 16 toward the smoke sensing photocell 17. The secondary scattering from area 16* diffuses most of the light in directions other than toward the photocell 17, but because of the large scattering areas involved light reaches the photocell 17 equivalent to that scattered by smoke of a predetermined density. The predetermined density, for example, may be that density of smoke which attenuates a beam of light 2% in one foot.

The foregoing primary and secondary scattering arrangement has the advantage that the flag by virtue of its large surface will scatter light from a relatively large, and hence more representative cross section of the light beam, and will scatter such representative sample despite manufacturing variations in the light source 7 such as the orientation of light emitting element relative to its base, and the associated reflective or transmissive optics. More over changes in the geometric relationships between the light source 7, flag position 30* and smoke sensing photocell 17 do not cause large changes in the secondarily scattered light ultimately reaching the photocell by reason of the fact that the primary scattering blankets the secondary scattering area and scatters light beyond the secondary area. Thus variations in the geometric relations mentioned merely change the light falling outside the secondary scattering area while maintaining a representative intensity in the secondary area viewed by the photocell 17.

Preferably the bell crank 31 and the flag extending at right angles thereto are molded integrally of a homogeneously colored plastic such as glass filled nylon with a dull grey surface. Such a material has distinct advantages over a treated metal surface such as reliable reproducibility of light scattering characteristic and maintenance of that characteristic over long periods of time.

Figure 3:
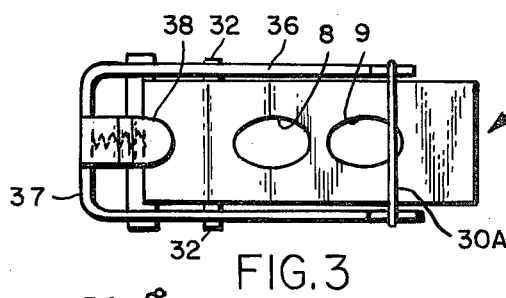
FIGS. 3 and 4 are respectively a plan view and side elevation of another form of the invention.
Figure 4:
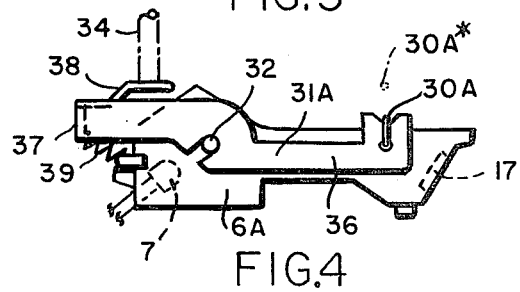

However, as exemplified by the smoke simulator of FIGS. 3 and 4 a relatively large steel wire with a natural dull grey oxidized finish may be used. By a large wire is meant a wire of 18 or more mil diameter as compared to the 5 mil or smaller of prior test wires. An 18 mil diameter wire is not fragile nor difficult to handle in manufacture and intercepts a fairly representative cross section of an exciting light beam. Such a wire flag 30A is shown in FIGS. 3 and 4 bridging the arms of a lever 31A pivoted at 32 on an optical block 6A containing a single, smoke sensing photocell 17 in a passage 9 and an LED 7 in a passage 8. The lever 31A is formed of sheet metal in a U-shape with two parallel arms 36, a connecting end 37 and a tongue 38 extending along the U from the connecting end for engagement by a manually operated plunger 34 such as is shown in FIG. 2. A spring 39 normally urges the wire 30A against the optical block 6A out of the beam of light from the LED 7, as is the case with the detector of FIGS. 1 and 2. When the plunger 34 and lever 31A are actuated the wire moves to a position 30A* in which it scatters light to secondary scattering areas such as the area 16* of FIG. 2 thereby indirectly exciting the smoke sensing cell 17 as previously described.

Figure 5:
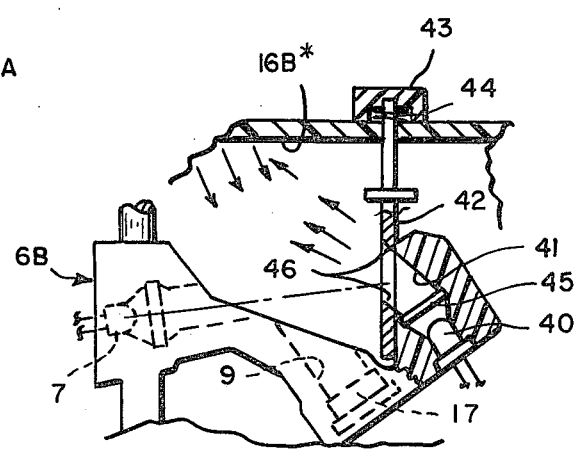
FIG. 5 is a section like FIG. 2 of a further form of the invention.

FIG. 5 illustrates a form of the invention in which an independent light source 40 performs the function of the primary light scatterers 30 and 30A of FIGS. 1 to 4. As shown, the light source 40, which is an LED, is located in a light passage 41 of an optical block 6B adjacent the passage 9 from the smoke sensing photocell 17. The previously described exciter lamp 7 is also provided in the block. Normally light from the LED 40 is masked by a shutter carried on a plunger 42 actuated by a manually operated button 43 external of a smoke detector cover 16B similar to that of cover 16 in FIGS. 1 and 2. When the plunger 42 is depressed against a spring 44 until the shutter aperture passes the LED 40 source light, the light, previously diffused in transmission through the passage 41 by a diffusion disk 42, is spread over the various internal areas such as the underside area 16B of the cover 16 shown in FIGS. 1 and 2. Secondary scattering from the area 16B excites the smoke sensing cell 17 as previously explained.

It should be understood that the present disclosure is for the purpose of illustration only and that this invention includes all modifications and equivalents which fall within the scope of the appended claims.

I claim:
1. A unitary smoke alarm comprising:
 a smoke accessible dark chamber at least partially enclosed by a light scattering wall,
 a source of light projected on a path in the chamber,
 a photocell disposed adjacent the chamber to view an area within the chamber and responsive to light scattered by particles in the path within the chamber to generate an alarm, and
 actuated light directing means outside the view of the photocell having a first condition in which it is ineffective to direct light to the area viewed by the photocell, and a second condition for directing light onto the viewed chamber area in the enclosure for secondary light scattering from said light scattering wall toward the photocell thereby to simulate particles in the chamber, said means in said second condition being substantially ineffective to direct light density to the photocell, and said photocell being responsive to light scattered by particles when the means is in said first condition.
2. A detector according to claim 1 wherein the actuated means comprises a primary light scattering surface moveable from outside the light path to a position in the light path substantially out of the photocell view.
3. A detector according to claim 2 wherein the viewed secondary light scattering area is substantially larger than the primary scattering surface.
4. A detector according to claim 2 wherein the light scattering capacity of the secondary light scattering area toward the photocell is substantially greater than that of the moveable scattering surface.
5. A detector according to claim 2 wherein the secondary light scattering area diffuses light substantially over the photocell area.
6. A detector according to claim 2 wherein the secondary light scattering area exceeds the view of the photocell so that variations in primary scattered light due to light source direction and scattering means position do not substantially affect the photocell response.
7. A detector according to claim 2 wherein the primary light scattering surface is adapted to scatter light over a secondary light scattering area exceeding the view of the photocell in varying spacial relationships of the light source and secondary surface.
8. A detector according to claim 2 wherein the light scattering surface comprises a homogeneously colored plastic material.
9. A detector according to claim 8 wherein the surface is dull grey glass-filled nylon.
10. A detector according to claim 1 wherein the actuated means comprises a lever pivoted on an optical block mounting the photocell.
11. A detector according to claim 1 wherein the actuated means comprises a lever pivoted on an optical block mounting the light source.
12. A detector according to claim 1 wherein the actuated means comprises a U-shaped yoke pivoted on opposite sides of an optical block and carrying a wire bridging the yoke.
13. A detector according to claim 1 comprising means extending externally of the detector for manual operation.
14. A detector according to claim 13 including stop means limiting movement of the actuating means.

* * * * *

UNITED STATES PATENT AND TRADEMARK OFFICE
CERTIFICATE OF CORRECTION

PATENT NO. : 4,166,698

DATED : September 4, 1979

INVENTOR(S) : Donald F. Steele

It is certified that error appears in the above-identified patent and that said Letters Patent are hereby corrected as shown below:

Claim 1, column 4, line 21, change "density"

to -- directly --.

Signed and Sealed this

Fifteenth Day of April 1980

[SEAL]

Attest:

SIDNEY A. DIAMOND

Attesting Officer     Commissioner of Patents and Trademarks